(12) United States Patent
Wu et al.

(10) Patent No.: US 8,394,758 B2
(45) Date of Patent: Mar. 12, 2013

(54) TUMOR-TARGETING PEPTIDES AND USES THEREOF

(75) Inventors: Han-Chung Wu, Taipei (TW); De-Kuan Chang, Taoyuan County (TW); Chien-Yu Chiu, Taipei (TW)

(73) Assignee: Academia Sinica, Taipei (TW)

( * ) Notice: Subject to any disclaimer, the term of this patent is extended or adjusted under 35 U.S.C. 154(b) by 591 days.

(21) Appl. No.: 12/607,334

(22) Filed: Oct. 28, 2009

(65) Prior Publication Data
US 2010/0119444 A1 May 13, 2010

Related U.S. Application Data

(60) Provisional application No. 61/109,314, filed on Oct. 29, 2008.

(51) Int. Cl.
| | |
|---|---|
| *A61K 38/00* | (2006.01) |
| *A61K 38/04* | (2006.01) |
| *A61K 51/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |

(52) U.S. Cl. ........ 514/1.1; 514/21.5; 530/327; 530/333; 424/1.69; 424/184.1

(58) Field of Classification Search .................. None
See application file for complete search history.

(56) References Cited

U.S. PATENT DOCUMENTS

| | | | | |
|---|---|---|---|---|
| 8,039,440 | B2 * | 10/2011 | Peled et al. | 514/21.5 |
| 2003/0166004 | A1 * | 9/2003 | Gyuris et al. | 435/7.1 |
| 2008/0193510 | A1 | 8/2008 | Wu et al. | |

FOREIGN PATENT DOCUMENTS

| | | | |
|---|---|---|---|
| WO | WO 03037172 | * | 5/2003 |
| WO | WO 03072599 | * | 9/2003 |

OTHER PUBLICATIONS

Dickerson, Matthew B., The protein and peptide mediated syntheses of non-biologically-produced oxide materials, Paper for doctoral degree, (2007), School Materials Science and Engineering, Georgia Institute of Technology.
Willerth et al., Stephanie M., Rationally designed peptides for controlled release of nerve growth factor from fibrin matrices, J. Biomedical Materials Research (2006, online publication), 80(1): p. 13-23.
Kuo et al., Identification of Oral Cancer-Targeted Peptides by in vivo Phage Display and Ligand-targeted Therapy for Anti-angiogenic Therapy, Student Thesis of National Taiwan University, 2004.
Willerth et al., "Rationally Designed Peptides for Controlled Release of Nerve Growth Factor from Fibrin Matrices," Journal of Biomedical Materials Research Parts A, vol. 80(1):13-23 (2006).
Matthew B. Dickerson, School of Material Science and Engineering, Georgia Institute of Technology Paper for Doctoral Degree, titled "The Protein and Peptide Mediated Syntheses of Non-Biologically-Produced Oxide Materials," (Jul. 9, 2007; https://smartech.gatech.edu/bitstream/1853/24704/1/Dickerson_Matthew_B_200708_phd.pdf).
Chang et al., "Antiangiogenic Targeting Liposomes Increase Therapeutic Efficacy for Solid Tumors," J. Biol. Chem. 284(19):12905-12916 (2009).

* cited by examiner

*Primary Examiner* — Maury Audet
(74) *Attorney, Agent, or Firm* — Wolf, Greenfield & Sacks, P.C.

(57) ABSTRACT

Tumor targeting peptides and uses thereof in tumor diagnosis and treatment.

20 Claims, No Drawings

TUMOR-TARGETING PEPTIDES AND USES THEREOF

RELATED APPLICATION

This application claims priority to U.S. Provisional Application No. 61/109,314, filed on Oct. 29, 2008, the content of which is hereby incorporated by reference in its entirety.

BACKGROUND OF THE INVENTION

Tumor angiogenesis refers to the proliferation of a blood vessel network that supplies nutrients and oxygen to cancerous tissues and removes waste products from them. Angiogenesis is involved in development of all solid tumors, including both tumor growth and metastasis. Given its fundamental function in tumor development, angiogenesis is an ideal target for solid tumor treatment.

Early diagnosis and targeted drug delivery significantly improve efficacy of tumor therapy. It is of particular importance to identify tumor targeting agents, such as those that have specific binding activity to new blood vessels formed in tumor angiogenesis.

SUMMARY OF THE INVENTION

The present invention is based on an unexpected discovery that a number of peptides, including SVSVGMKPSPRP (SEQ ID NO:1), NYLHNHPYGTVG (SEQ ID NO:2), SNPFSKPYGLTV (SEQ ID NO:3), GLHESTFTQRRL (SEQ ID NO:4), YPHYSLPGSSTL (SEQ ID NO:5), SSLEPWHRTTSR (SEQ ID NO:6), and LPLALPRHNASV (SEQ ID NO:7), specifically target blood vessels in tumor tissues, thereby facilitating drug delivery to tumor sites.

Accordingly, one aspect of this invention features a tumor-targeting conjugate containing (a) a reporting agent (e.g., a radioactive molecule) or an anti-tumor drug (e.g., doxorubicin) and (b) a peptide including any of the amino acid sequences of SEQ ID NOs: 1-7. The tumor-targeting conjugate can further contain a vehicle carrier, e.g., a liposome that encapsulates the reporting agent or the anti-tumor drug.

Another aspect of the invention is a method for solid tumor diagnosis in a subject (e.g., a human). This method includes (i) contacting a tissue of a subject with the tumor targeting conjugate described above that contains a reporting agent, the tissue being suspected of containing tumor matter, (ii) detecting a signal released from the reporting agent, and (iii) determining the presence or absence of tumor matter in the subject based on intensity of the signal. An elevated signal intensity as compared to that obtained from a tumor-free tissue indicates that the subject has solid tumor (e.g., lung cancer, oral cancer, colon cancer, breast cancer, prostate cancer, pancreatic cancer, and liver cancer).

In yet another aspect, the present invention provides a targeted drug delivery method by administering to a subject (e.g., a human patient) with a solid tumor an effective amount of the conjugate described above that contains an anti-tumor drug. "An effective amount" as used herein refers to the amount of the conjugate for delivering each active agent included therein to a solid tumor site so that the active agent confers therapeutic effect on the subject, either alone or in combination with one or more other active agents. Effective amounts vary, as recognized by those skilled in the art, depending on route of administration, excipient choice, and co-usage with other active agents.

Also within the scope of this invention is use of any of the tumor targeting conjugates described above for solid tumor diagnosis/treatment or for the manufacture of a medicament for diagnosing/treating solid tumor.

The details of one or more examples of the invention are set forth in the description below. Other features or advantages of the present invention will be apparent from the following detailed description of several embodiments, and also from the appended claims.

DETAILED DESCRIPTION OF THE INVENTION

The present invention relates to a number of tumor-targeting peptides, i.e., a peptide having one of the amino acid sequences shown below (see also Chang et al *J. Biol. Chem.* 284 (19):12905-12916, 2009):

| | |
|---|---|
| SVSVGMKPSPRP, | (SEQ ID NO: 1) |
| NYLHNHPYGTVG, | (SEQ ID NO: 2) |
| SNPFSKPYGLTV, | (SEQ ID NO: 3) |
| GLHESTFTQRRL, | (SEQ ID NO: 4) |
| YPHYSLPGSSTL, | (SEQ ID NO: 5) |
| SSLEPWHRTTSR, and | (SEQ ID NO: 6) |
| LPLALPRHNASV, | (SEQ ID NO: 7) |

The term "peptide" used herein refers to a polymer composed of two or more amino acid monomers and is shorter than a protein. Preferably, each of the tumor-targeting peptides described herein includes up to 50 (e.g., up to 20 or 30) amino acids. These tumor-targeting peptides can be prepared by conventional methods, i.e., chemical synthesis or recombinant technology.

The tumor-targeting peptides described herein particularly target tumor neovasculature. See US Patent Publication 2008/0193510 and Chang et al., *J. Biol. Chem.* 284 (19):12905-12916 (2009). Thus, when conjugated with a reporting agent (e.g., an imaging molecule) or an anti-tumor agent, it directs the agent to a tumor site, thereby facilitating tumor diagnosis (both in vivo and in vitro) or treatment. As used herein, "conjugated" means two entities are associated, preferably with sufficient affinity that the therapeutic/diagnostic benefit of the association between the two entities is realized. Conjugated can include covalent or noncovalent bonding as well as other forms of association, such as entrapment, e.g., of one entity on or within the other, or of either or both entities on or within a third entity, such as a micelle.

In one example, one of the tumor-targeting peptides described above is conjugated with a reporting agent to form a diagnosing conjugate used in both in vivo and in vitro detection of tumor mass. The reporting agent can be a tumor-imaging molecule, i.e., a radioactive molecule, a radiopharmaceutical, or an iron oxide particle. Radioactive molecules suitable for in vivo imaging include, but are not limited to, $^{122}$I, $^{123}$I, $^{124}$I, $^{125}$I, $^{131}$I, $^{18}$F, $^{75}$Br, $^{76}$Br, $^{76}$Br, $^{77}$Br, $^{211}$At, $^{225}$Ac, $^{177}$Lu, $^{153}$Sm, $^{186}$Re, $^{188}$Re, $^{67}$Cu, $^{213}$Bi, $^{212}$Bi, $^{212}$Pb, and $^{67}$Ga. Exemplary radiopharmaceuticals suitable for in vivo imaging include $^{111}$In Oxyquinoline, $^{131}$I Sodium iodide, $^{99m}$Tc Mebrofenin, and $^{99m}$Tc Red Blood Cells, $^{123}$I Sodium iodide, $^{99m}$Tc Exametazime, $^{99m}$Tc Macroaggregate Albumin, $^{99m}$Tc Medronate, $^{99m}$Tc Mertiatide, $^{99m}$Tc Oxidronate, $^{99m}$Tc Pentetate, $^{99m}$Tc Pertechnetate, $^{99m}$Tc Sestamibi, $^{99m}$Tc Sulfur Colloid, $^{99m}$Tc Tetrofosmin, Thallium- 201, and Xenon-133. The reporting agent can also be a dye, e.g., a fluorophore, which is useful in detecting tumor mass in tissue samples.

In another example, one of the tumor-targeting peptides described herein is conjugated with an anti-tumor drug to form a treatment conjugate. The drug can be a chemotherapy agent, such as drugs that stop DNA building block synthesis (e.g., methotrexate, fluorouracil, hydroxyurea, and mercaptopurine), drugs that directly damage DNA (e.g., cisplatin, daunorubicin, doxorubicin, and etoposide), drugs that affect mitotic spindle synthesis or breakdown (e.g., vinblastine, vincristine, and pacitaxel), or drugs that disrupt angiogenesis (e.g., anti-VEGF antibody, angiostatin, endostatin, and tumstatin). Alternatively, the anti-tumor drug can be a radiotherapy agent (e.g., $^{90}Y$, $^{125}I$, $^{188}Re$, $^{111}In$ DTPA, or $^{131}I$ Sodium iodide).

In any of the diagnosing and treatment conjugates described above, the tumor-targeting peptide can be linked directly to a reporting molecule or an anti-tumor drug via methods known in the art. Alternatively, the tumor-targeting peptide is linked to a vehicle carrier, which is associated with the reporting molecule/anti-tumor drug and/or the tumor targeting peptide. In one example, the vehicle carrier encapsulates the reporting molecule or the anti-tumor drug. Vehicle carriers include, but are not limited to, micelle, liposome (e.g., cationic liposome), nanoparticle, microsphere, or biodegradable polymer. A tumor-targeting peptide can be tethered to a vehicle carrier by a variety of linkages (e.g., a disulfide linkage, an acid labile linkage, a peptide-based linkage, an oxyamino linkage, or a hydrazine linkage). The reporting molecule or anti-tumor drug encapsulated within the vehicle can be associated with lipophilic molecules, which can aid in the delivery of the reporting molecule/anti-tumor drug to the interior of the vehicle.

In a preferred example, a tumor-targeting peptide is linked to a liposome (as a vehicle carrier) that encapsulates an agent (e.g., a radioactive molecule or an anti-tumor drug) to be delivered to a tumor site. The term "liposome" refers to vesicles comprised of one or more concentrically ordered lipid bilayers, which encapsulate an aqueous phase. The aqueous phase typically contains an agent to be delivered to a tumor site. Upon reaching a tumor site, the liposome fuses with the plasma membranes of local tumor cells or tumor blood vessel cells, thereby releasing the agent into the cytosol. Alternatively, the liposome is endocytosed or otherwise taken in by the tumor cells or of tumor blood vessel cells as the content of a transport vesicle (e.g., an endosome or phagosome). Once in the transport vesicle, the liposome either degrades or fuses with the membrane of the vesicle and releases its contents. Liposome membranes can be constructed so that they become destabilized when the nearby environment becomes acidic (see, e.g., PNAS 84:7851, 1987; Biochemistry 28:908, 1989). Thus, when liposomes enter a target cell, they become destabilized to release their encapsulated contents. This destabilization process is termed fusogenesis. Dioleoylphosphatidylethanolamine (DOPE) is commonly used to facilitate this process.

A variety of methods are available for preparing liposomes. See, e.g., Szoka et al., Ann. Rev. Biophys. Bioeng. 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer & Bangham, Biochim. Biophys. Acta 443:629-634 (1976); Fraley, et al., PNAS 76:3348-3352 (1979); Hope et al., Biochim. Biophys. Acta 812:55-65 (1985); Mayer et al., Biochim. Biophys. Acta 858:161-168 (1986); Williams et al., PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vehicles and ether fusion methods, all of which are well known in the art.

Any of the tumor imaging or treatment conjugates described herein can be mixed with a pharmaceutically acceptable carrier to form a pharmaceutical composition. "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof To use any of the conjugates described herein for tumor diagnosis or treatment, the conjugate can be administered orally, parenterally, topically, rectally, nasally, buccally, vaginally, via an implanted reservoir, or via inhalation spray. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) or suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets/capsules for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. An oxadiazole compound-containing composition can also be administered in the form of suppositories for rectal administration.

When a diagnosing conjugate described above that contains an imaging agent is used for in vivo tumor imaging, a suitable amount of the conjugate (e.g., containing about 20 μg of a tumor-targeting peptide and about 400 MBq of a radioactive molecule) can be injected to a suspected cancer patient. The patient is then subjected to scintigraphy at suitable periods, e.g., 2 h, 4 h, 24 h, 48 h, and/or 72 h, after injection. Radioactivities of the whole body and the regions of interest are normalized against background activity and the presence/absence of tumor matter can be determined based on the results thus obtained.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Targeting Oral Cancer with Tumor-Targeting Peptides

SAS cells (an oral cancer cell line) were injected subcutaneously (s.c.) into the dorsolateral flanks of SCID mice (4-6 weeks of age) to form oral cancer xenografts. Mice bearing xenografts having a size around 500 mm³ were injected intravenously (i.v.) with the peptide-display phage clones shown in Table 1 below through their tail veins. Also shown in Table 1 are the peptides displayed on the surface of these phage clones.

TABLE 1

Tested Peptide-display Phage Clones and Peptides Expressed Therein

| Peptide-Display Phage Clones | Displayed Peptides | SEQ ID Nos |
|---|---|---|
| IVO-2 | SVSVGMKPSPRP (PIVO-2) | SEQ ID NO: 1 |
| IVO-5 | NYLHNHPYGTVG (PIVO-5) | SEQ ID NO: 2 |
| IVO-8 | SNPFSKPYGLTV (PIVO-8) | SEQ ID NO: 3 |
| IVO-12 | GLHESTFTQRRL (PIVO-12) | SEQ ID NO: 4 |
| IVO-24 | YPHYSLPGSSTL (PIVO-24) | SEQ ID NO: 5 |
| IVO-25 | SSLEPWHRTTSR (PIVO-25) | SEQ ID NO: 6 |
| IVO-29 | LPLALPRHNASV (PIVO-29) | SEQ ID NO: 7 |

Eight minutes after the injection, the phage-treated SCID mice were perfused with 50 ml PBS to wash away phage particles unbound to tissues. Normal organs (e.g., lung, heart, brain) and tumor mass were removed from the mice, weighed, washed with PBS, and homogenized to release tissue-bound phage particles, if any. The released phage particles were titered using bacterium ER2738 (New England BioLabs, MA, USA) grown on IPTG-X-gal-containing agar plates, and amplified in the same bacterium following the manufacturer's protocol.

Results obtained from this study show that all of the tested phage clones accumulated in tumor mass at levels much higher than those in normal organs, i.e., lung, heart, and brain, indicating that the peptides displayed by these phage clones specifically bound to tumors.

EXAMPLE 2

Targeting Lung Tumor with Phage Clones IVO-2, IVO-8, and IVO-24

H460 cells (a lung cancer cell line) were injected subcutaneously (s.c.) into the dorsolateral flanks of SCID mice (4-6 weeks of age) to form lung cancer xenografts. Each of phage clones IVO 2, IVO 8, and IVO 24, displaying peptide SVSVGMKPSPRP (SEQ ID NO:1), SNPFSKPYGLTV (SEQ ID NO:3), and YPHYSLPGSSTL (SEQ ID NO:5), respectively, was injected (i.v.) into the tail veins of the mice bearing the xenografts (~100 mm³), either alone or with 100 μg synthetic peptides SVSVGMKPSPRP (SEQ ID NO:1), SNPFSKPYGLTV (SEQ ID NO:3), or YPHYSLPGSSTL (SEQ ID NO:5). Normal organs and tumor mass were removed from these mice and processed as described in Example 1 above. The phage titers in the normal organs and tumor mass were determined following the procedure also described in Example 1.

All of phage clones IVO-2, IVO-8, and IVO-24 were accumulated in the lung tumor xenografts but not in normal organs. Synthetic peptide SVSVGMKPSPRP (SEQ ID NO:1) inhibited accumulation of phage clone IVO 2 (displaying the peptide of SEQ ID NO:1), but not the other two phage clones, in tumor mass. Similarly, synthetic peptides SNPFSKPYGLTV (SEQ ID NO:3) and YPHYSLPGSSTL (SEQ ID NO:5) inhibited accumulation of phage clones IVO-8 (displaying the peptide of SEQ ID NO:3) and IVO-24 (displaying the peptide of SEQ ID NO:5), respectively, in tumor mass. These results demonstrate that the specific binding between the phage clones and tumor tissues is mediated by the peptides displayed thereon.

The accumulation of the phage clones in tumor mass was further examined by an immuno-staining assay, using an anti-M13 phage monoclonal antibody (Amersham Biosciences, Uppsala, Sweden). Briefly, after injection of the phage clones, normal organ samples and tumor samples were obtained, each divided into two parts. Bound phage particles were released from one part of the samples and titered using bacterium ER2738. The other part of each of the samples was embedded in Optimal Cutting Temperature (OCT, Tissue-Tek, NL, USA). The OCT-embedded samples (frozen) were sectioned (5 micron) and transferred to cold PBS. The sections were fixed with acetone-methanol (1:1) on slides, washed with PBS, and immersed in a blocking buffer (1% BSA in PBS) for 1 h. Then, the slides were incubated with rat anti-mouse CD31 antibody (an antibody recognizing blood vessels; BD Pharmingen, MA, USA.) and rabbit anti-rat Ig antibody (Stressgen, Canada), and immersed in Rhodamine labeled goat anti-rabbit Ig antibody (Jackson ImmunoResearch, PA, USA). The slides were further incubated with mouse anti-M13 phage monoclonal antibody (Amersham Biosciences, Uppsala, Sweden), then with FITC-labeled goat anti-mouse Ig antibody (Jackson ImmunoResearch, PA, USA), and finally immersed in a solution containing Hoechst 33258 (Molecular Probe, OR, USA). After being washed and mounted with a mounting medium (Vector, Calif., USA), the slides were examined under a Leica Confocal Microscope (TCS-SP5-AOBS). Images of the slides were processed with the Leica Application Suite Advanced Fluorescence software.

Immuno-reactivity was observed only in lung tumor mass, but not in normal lung tissues, indicating that the tested phage clones, i.e., IVO-2, IVO-8, and IVO-24, specifically bound to lung tumor mass. Again, synthetic peptides SVSVGMKPSPRP (SEQ ID NO:1), SNPFSKPYGLTV (SEQ ID NO:3), and YPHYSLPGSSTL (SEQ ID NO:5) blocked binding of phage clones IVO-2, IVO-8, and IVO-24, respectively, to lung tumor tissues.

Results obtained from the immuno-staning assay described above indicate that the three phage clones were co-localized with the anti-CD31 antibody in the lung tumor xenografts, but not in normal organs. These results demonstrate that the three peptides displayed on the test phage clones specifically recognize tumor neovasculature.

EXAMPLE 3

Targeting Various Tumors with Phage Clones IVO-8 and IVO-24

Xenografts of human lung cancer, colon cancer, breast cancer, prostate cancer, pancreatic cancer, and liver cancer were formed in SCID mice, using cancer cell lines H460, HCT116, BT483, PC3, PaCa and Mahlavu, respectively. Phage clones IVO-8 and IVO-24 and a control phage clone were injected into the tail veins of these SCID mice. The tumor xenografts and normal organs (i.e., brain, heart, and lung) were removed from the mice and subjected to examination of phage particle accumulation, following the method described in Example 1 above.

Both phage clones IVO-8 and IVO-24, but not the control phage clone, were found to be accumulated in tumor tissues but not normal organs. This result indicates that the two peptides displayed on IVO-8 and IV024 target various types of tumors.

EXAMPLE 4

Specific Binding of Phage Clones IVO-2, IVO-8 and IVO-24 to Human Endothelia Cells and Blood Vessels in Various Human Surgical Cancer Specimens Human vascular endothelial cells (HUVECs) were plated and grown to approximately 80% confluence on coverslips. The cells were then treated with 20 ng/ml VEGF (B&D Systems, MN, USA) and 2 ng/ml bFGF (PEPROTECH, London, UK) for 48 h. The treated and untreated HUVECs were washed with serum-free M199 containing 3% BSA, incubated in a blocking buffer for 30 min at 4° C., and then treated with phage clones IVO-8 and IVO-24, and a control phage clone at 4° C. for 1 h. Afterwards, the cells were washed and fixed in 3% formaldehyde for 10 min, incubated with mouse anti-M13 mAb (Amersham Biosciences) for 1 h, then with FITC-labeled anti-mouse Ig Ab (Jackson ImmunoResearch), and finally stained with Hoechst 33258. The coverslips containing the stained HUVECs were washed and mounted. Images obtained thereby were processed using the SimplePCI software (C-IMAGING, PA, USA).

The control phage clone showed no binding activity to HUVECs and no phage clones were found to be bound to HUVECs not treated by VEGF. By contrast, both phage clones IVO-8 and IVO-24 bound to VEGF-stimulated HUVECs. These results indicate that the peptides displayed on the two phage clones specifically bound to VEGF-stimulated human endothelial cells, the main type of cells in tumor blood vessels.

Next, the binding activity of phage clones IVO-2, IVO-8, and IVO-24 to surgical cancer specimens were examined. Surgical specimens (containing normal tissues or tumor mass) obtained from patients suffering from breast cancer, lung cancer, colon cancer, liver cancer, oral cancer, or pancreatic cancer were sectioned, transferred to slides, incubated in a blocking buffer for 30 min, and treated with phage clones IVO-2, IVO-8 and IVO-24, and the control clone in the presence of biotinylated UEA-1, an agent for staining blood vessels (see Kalka et al., Proc. Natl. Acad. Sci. USA, 97:3422-3427, 2000). After being washed, the slides containing the sections were incubated with mouse anti-M13 mAb and FITC-conjugated streptavidin (Pierce, Ill., USA) for 1 h, and then incubated with phycoerythrin-conjugated goat anti-mouse Ig Ab (Jackson ImmunoResearch, PA, USA). These slides were examined under a Zeiss Axiovert 200M inverted microscope and the images were processed using a MetaMorph software (Molecular Devices, PA, USA).

As shown in Table 2 below, phage clones IVO-2, IVO-8 and IVO-24, but not the control clone, were found in the surgical specimens containing tumor mass. These phage clones, however, did not bind to surgical specimens containing normal tissues. The results obtained from this study also show that phage clones IVO-2, IVO-8, and IVO-24 were co-localized with UEA-1. Taken together, this study demonstrated that the peptides displayed on IVO-2, IVO-8, and IVO-24 are specific to blood vessels in tumor mass.

TABLE 2

Summary of phage-positive surgical specimens derived from human cancer patients

| Samples | cancer | | | | | |
| --- | --- | --- | --- | --- | --- | --- |
|  | Breast | Lung | Colon | Liver | Oral | Pancreas |
| n | 10 | 10 | 10 | 10 | 10 | 10 |
| IVO-2 positive | 8 | 6 | 7 | 4 | 6 | 7 |
| IVO-8 positive | 5 | 7 | 7 | 6 | 7 | 7 |
| IVO-24 positive | 6 | 6 | 6 | 5 | 7 | 8 |

In sum, the results shown above indicate that the three phage clones listed in Table 2, particularly, the peptide displayed on these phage clones, can be used for tumor diagnosis.

EXAMPLE 5

Treating Cancer with Tumor-Targeting Peptide-Conjugated Liposomal Doxorubicin

Peptides SVSVGMKPSPRP (PIVO-2, SEQ ID NO:1), SNPFSKPYGLTV (PIVO-8, SEQ ID NO:3), and YPHYSLPGSSTL (PIVO-24, SEQ ID NO:5) were synthesized chemically and purified by reverse-phase-high-performance liquid chromatography. Each of the peptides thus obtained had a purity greater than 95%. When necessary, these peptides were linked with FITC or biotin at their N-terminal.

Peptide-conjugated liposomes that encapsulate doxorubicin ("Peptide-LD") were prepared following the method described in Lee et al., Cancer Res. 67:10958-10965, 2004 and Lo et al., Mol. Cancer. Ther. 7:579-589, 2008. Briefly, a peptide was coupled to NHS-PEG-DSPE [N-hydroxysuccinimido-carboxyl-polyethylene glycol (PEG; average molecular weight, 3000)-derived distearoylphosphatidylethanolamine] (NOF Corporation, Tokyo, Japan) at a molar ratio of 1:1.5. Completion of the conjugating reaction was confirmed by measuring the remaining amino groups using a Trinitrobenzenesulfonate (TNBS) reagent (AFSA 1966). Peptidyl-PEG-DSPE was conjugated to pre-formed doxorubicin-entrapped liposomes after co-incubation at a temperature higher than the transitional temperature of the lipid bilayer. See Zalipsky et al., Bioconjugate Chemistry 8:111-118, 1997. The resultant Peptide-LD contained ~500 peptide molecules per liposome, as determined by the method described in Kirpotin et al., Biochemistry 36:66-75, 1997.

Five types of xenografts, i.e., lung cancer, breast cancer, liver cancer, pancreatic cancer, and colon cancer, were induced in SCID mice with cancer cell lines of H460, BT483, Mhlavu, PaCa, and HCT116, respectively, following the method described in Example 4 above. The mice bearing tumors in the size of ~100 mm$^3$ were randomly assigned to six groups, each treated, through their tail veins, with (1) PIVO-2-conjugated liposomal doxorubicin (PIVO-2-LD), (2) PIVO-8-conjugated liposomal doxorubicin (PIVO-8-LD), (3) PIVO-24-conjugated liposomal doxorubicin (PIVO-24-LD), (4) liposomal doxorubicin (LD), (5) free doxorubicin (FD), or (6) saline control (PBS), at a doxorubicin dosage of 1 mg/kg, twice a week for four weeks. Mouse body weights and tumor lengths/widths were measured twice a week with calipers. The volume of a tumor was calculated using the formula: length×(width)×0.52.

Results obtained from this study indicate that LD was more effective than FD in reducing the volumes of the five xenografts. Surprisingly, the peptide-conjugated LDs, i.e., PIVO-2-LD, PIVO-8-ID, and PIVO-24-LD, showed significantly higher activity than LD in reducing tumor volumes.

Next, the histopathology of tumor tissues in the mice of the six groups was examined by H&E staining In the group treated with PIVO-2-LD, PIVO-8-ID, or PIVO-24-LD, a significantly large necrotic/apoptotic area (combined) was observed in their tumor xenografts. In contrast, only a moderate necrotic/apoptotic area (combined) was detected in the group treated with LD or FD. No necrotic/apoptotic area was found in the PBS treated group.

Finally, the effect of peptide-conjugated LDs in reducing the levels of tumor blood vessels was explored. Tumor tissues were removed from each mouse of the six groups, fixed with 4% paraformaldehyde, and embedded in paraffin. To detect blood vessels, the embedded tissues were stained with Lycopersicon esculentum (tomato) lectin conjugated to biotin (Vector, Calif., USA) and then with streptavidin-conjugated rhodamine (Pierce, Ill., USA). Results thus obtained show that tumor blood vessels were significantly reduced in mice treated with PIVO-2-LD, PIVO-8-ID, and PIVO-24-LD as compared with mice treated with LD and FD.

In sum, the data described above demonstrate that liposomal doxorubicin conjugated with PIVO-2, PIVO-8, or PIVO-24 was more effective than liposomal doxorubicin and free doxorubicin in cancer treatment.

EXAMPLE 6

Targeted Drug Delivery with Peptide-Conjugated Liposomes

Non-small cell lung cancer xenografts (~300 mm$^3$) were induced in SCID mice following the method described in Example 2 above. These mice were treated with PIVO-2-LD, PIVO-8-LD, PIVO-24-LD, LD, and FD at a doxorubicin dose of 2 mg/kg and sacrificed 1 h, 4 h, or 24 h later. Blood samples were collected from the mice via submaxillary punctures and plasma samples were prepared therefrom. In addition, xenografts and normal organs were removed, part of them being homogenized to isolate cell nuclei. Doxorubicin was extracted either from the tumor tissue or from the nuclei following the method described in Laginha et al., Clin. Cancer Res. 11:6944-6949, 2005 and Mayer et al., J. Pharmacol. Exp. Ther. 280:1406-1414, 1997. The amount of doxorubicin was determined by spectrofluorometry at $\lambda_{ex}$ 485/20 nm and $\lambda_{em}$ 645/40 nm (Synergy HT Multi-Detection Microplate Reader, BioTek Instruments, Winooski, Vt. 05404 USA). Based on the amounts of doxorubicin in tumor tissues at different time points, concentration-time curves of doxorubicin were prepared and the areas under the curves from 0-48 hours ($AUC_{0-48\ hours}$) were determined.

As shown in Table 3 below, the levels of doxorubicin in the tumor issues of the mice treated with PIVO-2-LD, PIVO-8-LD and PIVO-24-LD were much higher than those in the tumor issues of the mice treated with FD and LD. More specifically, the mean intra-tumor doxorubicin level in the PIVO-2-LD-treated mice was 4.5- and 1.5-fold higher than that in the FD- and LD-treated mice; in the PIVO-8-LD-treated mice, the mean intra-tumor doxorubicin level was 4.8- and 1.6-fold higher than that of the FD- and LD-treated mice.

TABLE 3

Doxorubicin Levels in Tumor Tissues

| Formulation (2 mg/kg) | Tumor ($AUC_{0-48\ h}$ µg · h/g) | Nucleus ($AUC_{0-48\ h}$ µg · h/g) |
| --- | --- | --- |
| Free doxorubicin | 10.23 | 3.68 |
| Liposomal doxorubicin | 31.25 | 6.71 |
| PIVO-2-LD | 46.11 | 13.64 |
| PIVO-8-LD | 49.63 | 14.76 |
| PIVO-24-LD | 49.49 | 13.94 |

As indicated in Laginha et al., a nuclear doxorubicin level is an indicator of the bioavailability of this drug. Thus, nuclear doxorubicin is also named "bioavailable doxorubicin." As shown in Table 3 above, the levels of intra-tumor bioavailable doxorubicin in the mice treated with PIVO-2-LD, PIVO-8-LD and PIVO-24-LD are significantly higher that those in the mice treated with FD and LD.

Next, xenografts and normal organs were removed, sectioned, and the presence of doxorubicin in each section was examined by a Zeiss Axiovert 200M inverted microscope (with a 100 W HBO mercury light equipped with a 546/12 nm excitation filter set and a 590 nm emission filter set). Images of the tissue sections were captured with a Roper Scientific CoolSnap HQ CCD camera having a FLUAR 10×/0.50 NA lens.

In mice treated with PIVO-2-LD, PIVO-8-LD, and PIVO-24-LD, presence of doxorubicin was detected in the nuclei of tumor cells four hours after drug administration. The areas where presence of doxorubicin was detected were significantly larger in PIVO-2-LD, PIVO-8-LD and PIVO-24-LD-treated mice that those in mice treated with LD and FD.

Take together, the results obtained from this study demonstrate that peptides PIVO-2, PIVO-8, and PIVO-24 facilitated doxorubicin delivery to tumor sites.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A tumor-targeting conjugate comprising (1) a reporting agent or an anti-tumor drug and (2) a peptide containing an amino acid sequence selected from the group consisting of

```
       NYLHNHPYGTVG,      (SEQ ID NO: 2)
       SNPFSKPYGLTV,      (SEQ ID NO: 3)
       GLHESTFTQRRL,      (SEQ ID NO: 4)
       and
       LPLALPRHNASV.      (SEQ ID NO: 7)
```

2. The tumor-targeting conjugate of claim 1, wherein the peptide includes the amino acid sequence of SNPFSKPYGLTV (SEQ ID NO:3).

3. The tumor-targeting conjugate of claim 2, wherein the peptide is SNPFSKPYGLTV (SEQ ID NO:3).

4. The tumor-targeting conjugate of claim 1, further comprising a vehicle carrier.

5. The tumor-targeting conjugate of claim 4, wherein the vehicle carrier is a liposome, in which the reporting agent or the anti-cancer drug is encapsulated.

6. The tumor-targeting conjugate of claim 2, further comprising a liposome, in which the reporting agent or the anti-cancer drug is encapsulated.

7. The tumor-targeting conjugate of claim 1, wherein the conjugate contains a reporting agent, which is a radioactive molecule.

8. The tumor targeting conjugate of claim 1, wherein the conjugate contains an anti-cancer drug, which is doxorubicin.

9. A method for diagnosing solid tumor in a subject, said method comprising:

contacting a tissue of a subject with a tumor-targeting conjugate containing (1) a reporting agent and (2) a peptide including an amino acid sequence selected from the group consisting of NYLHNHPYGTVG (SEQ ID NO:2), SNPFSKPYGLTV (SEQ ID NO:3), GLHESTFTQRRL (SEQ ID NO:4), and LPLALPRHNASV (SEQ ID NO:7), wherein the tissue is suspected of containing tumor matter;

detecting a signal released from the reporting agent, and determining the presence or absence of tumor matter in the subject based on intensity of the signal, wherein a higher signal intensity obtained from the tumor-targeting conjugate comprising the amino acid sequence of SEQ ID NO:3 relative to that obtained from a tumor-free tissue indicates that the subject has solid tumor; and a higher signal intensity obtained from a tumor-targeting conjugate containing a peptide including the amino acid sequence selected from the group consisting of SEQ ID NO:2, 4, or 7 relative that obtained from a tumor-free tissue indicates that the subject has oral cancer.

10. The method of claim 9, wherein the peptide includes the amino acid sequence of SNPFSKPYGLTV (SEQ ID NO:3).

11. The method of claim 9, wherein the tumor targeting conjugate further contains a vehicle carrier.

12. The method of claim 11, wherein the vehicle carrier is a liposome, in which the reporting agent is encapsulated.

13. The method of claim 9, wherein the reporting agent is radioactive.

14. The method of claim 10, wherein the solid tumor is selected from the group consisting of lung cancer, oral cancer, colon cancer, breast cancer, prostate cancer, pancreatic cancer, and liver cancer.

15. A method for delivering an anti-tumor agent to a solid tumor, said method comprising administering to a subject in need thereof an effective amount of a tumor-targeting conjugate containing (1) an anti-tumor agent and (2) a peptide including the amino acid sequence selected from the group consisting of NYLHNHPYGTVG (SEQ ID NO:2), SNPFSKPYGLTV (SEQ ID NO:3), GLHESTFTQRRL (SEQ ID NO:4), and LPLALPRHNASV (SEQ ID NO:7), wherein the solid tumor is oral cancer when the subject is administered with a tumor-targeting conjugate containing a peptide including the amino acid sequence selected from the group consisting of SEQ ID No: 2, 4, or 7.

16. The method of claim 14, wherein the peptide includes the amino acid sequence of SNPFSKPYGLTV (SEQ ID NO:3).

17. The method of claim 15, wherein the tumor targeting conjugate further contains a vehicle carrier.

18. The method of claim 17, wherein the vehicle carrier is a liposome, in which the anti-tumor agent is encapsulated.

19. The method of claim 15, wherein the anti-tumor agent is doxorubicin.

20. The method of claim 16, wherein the solid tumor is selected from the group consisting of lung cancer, oral cancer, colon cancer, breast cancer, prostate cancer, pancreatic cancer, and liver cancer.

* * * * *

UNITED STATES PATENT AND TRADEMARK OFFICE
CERTIFICATE OF CORRECTION

PATENT NO. : 8,394,758 B2  
APPLICATION NO. : 12/607334  
DATED : March 12, 2013  
INVENTOR(S) : Han-Chung Wu et al.

Page 1 of 1

It is certified that error appears in the above-identified patent and that said Letters Patent is hereby corrected as shown below:

In the Claims:

Col. 13, Claim 1 should read:

"A tumor-targeting conjugate comprising (1) a reporting agent or an anti-tumor drug and (2) a peptide containing an amino acid sequence selected from the group consisting of TABLE-US-00005 NYLHNHPYGTVG, (SEQ ID NO: 2) SNPFSKPYGLTV, (SEQ ID NO: 3) GLHESTFTQRRL, (SEQ ID NO: 4) and LPLALPRHNASV (SEQ ID NO: 7)."

Col. 13-14, Claim 9 should read:

"A method for diagnosing solid tumor in a subject, said method comprising: contacting a tissue of a subject with a tumor-targeting conjugate containing (1) a reporting agent and (2) a peptide including an amino acid sequence selected from the group consisting of NYLHNHPYGTVG (SEQ ID NO:2), SNPFSKPYGLTV (SEQ ID NO:3), GLHESTFTQRRL (SEQ ID NO:4), and LPLALPRHNASV (SEQ ID NO:7), wherein the tissue is suspected of containing tumor matter; detecting a signal released from the reporting agent, and determining the presence or absence of tumor matter in the subject based on intensity of the signal, wherein a higher signal intensity obtained from the tumor-targeting conjugate comprising the amino acid sequence of SEQ ID NO:3 relative to that obtained from a tumor-free tissue indicates that the subject has solid tumor; and a higher signal intensity obtained from a tumor-targeting conjugate containing a peptide including the amino acid sequence selected from the group consisting of SEQ ID NO:2, 4, or 7 relative to that obtained from a tumor-free tissue indicates that the subject has oral cancer."

Signed and Sealed this  
Twenty-eighth Day of May, 2013

Teresa Stanek Rea  
*Acting Director of the United States Patent and Trademark Office*

SEQUENCE LISTING

<160> NUMBER OF SEQ ID NOS: 7

<210> SEQ ID NO 1
<211> LENGTH: 12
<212> TYPE: PRT
<213> ORGANISM: Artificial
<220> FEATURE:
<223> OTHER INFORMATION: Tumor-Targeting Peptide

<400> SEQUENCE: 1

Ser Val Ser Val Gly Met Lys Pro Ser Pro Arg Pro
1               5                   10

<210> SEQ ID NO 2
<211> LENGTH: 12
<212> TYPE: PRT
<213> ORGANISM: Artificial
<220> FEATURE:
<223> OTHER INFORMATION: Tumor-Targeting Peptide

<400> SEQUENCE: 2

Asn Tyr Leu His Asn His Pro Tyr Gly Thr Val Gly
1               5                   10

<210> SEQ ID NO 3
<211> LENGTH: 12
<212> TYPE: PRT
<213> ORGANISM: Artificial
<220> FEATURE:
<223> OTHER INFORMATION: Tumor-Targeting Peptide

<400> SEQUENCE: 3

Ser Asn Pro Phe Ser Lys Pro Tyr Gly Leu Thr Val
1               5                   10

<210> SEQ ID NO 4
<211> LENGTH: 12
<212> TYPE: PRT
<213> ORGANISM: Artificial
<220> FEATURE:
<223> OTHER INFORMATION: Tumor-Targeting Peptide

<400> SEQUENCE: 4

Gly Leu His Glu Ser Thr Phe Thr Gln Arg Arg Leu
1               5                   10

<210> SEQ ID NO 5
<211> LENGTH: 12
<212> TYPE: PRT
<213> ORGANISM: Artificial
<220> FEATURE:
<223> OTHER INFORMATION: Tumor-Targeting Peptide

<400> SEQUENCE: 5

Tyr Pro His Tyr Ser Leu Pro Gly Ser Ser Thr Leu
1               5                   10

<210> SEQ ID NO 6
<211> LENGTH: 12
<212> TYPE: PRT
<213> ORGANISM: Artificial
<220> FEATURE:
<223> OTHER INFORMATION: Tumor-Targeting Peptide

<400> SEQUENCE: 6

Ser Ser Leu Glu Pro Trp His Arg Thr Thr Ser Arg

```
                        -continued
1               5             10

<210> SEQ ID NO 7
<211> LENGTH: 12
<212> TYPE: PRT
<213> ORGANISM: Artificial
<220> FEATURE:
<223> OTHER INFORMATION: Tumor-Targeting Peptide

<400> SEQUENCE: 7

Leu Pro Leu Ala Leu Pro Arg His Asn Ala Ser Val
1               5                   10
```